United States Patent [19]
Ishikawa et al.

[11] Patent Number: 6,071,233
[45] Date of Patent: Jun. 6, 2000

[54] ENDOSCOPE

[75] Inventors: Masahiro Ishikawa, Hino; Koichi Kawashima, Tokyo; Tetsuya Yamamoto; Takayuki Suzuki, both of Hachioji; Tsutomu Okada, Kunitachi, all of Japan

[73] Assignee: Olympus Optical Co., Ltd., Tokyo, Japan

[21] Appl. No.: 09/152,805

[22] Filed: Sep. 14, 1998

[30] Foreign Application Priority Data

Oct. 31, 1997 [JP] Japan ................................. 9-300509
May 22, 1998 [JP] Japan ................................. 10-141116

[51] Int. Cl.$^7$ ........................................................ A61B 1/00
[52] U.S. Cl. ........................ 600/104; 600/129; 600/136; 600/153; 606/110; 606/113
[58] Field of Search ................................... 600/103, 104, 600/105, 107, 128, 129, 130, 136, 153, 156; 606/110, 113

[56] References Cited

U.S. PATENT DOCUMENTS

| | | | |
|---|---|---|---|
| 874,810 | 12/1907 | Wappler | 600/107 |
| 3,924,608 | 12/1975 | Mitsui | 600/107 |
| 4,224,929 | 9/1980 | Furihata | 600/107 |
| 4,237,871 | 12/1980 | Bonnet | 128/4 |
| 4,273,110 | 6/1981 | Groux | 128/6 |
| 4,807,593 | 2/1989 | Ito | 600/114 |
| 4,867,138 | 9/1989 | Kubota et al. | 600/107 |
| 5,167,220 | 12/1992 | Brown | 128/4 |
| 5,190,542 | 3/1993 | Nakao et al. | 606/47 |
| 5,213,092 | 5/1993 | Uram | 128/4 |
| 5,325,847 | 7/1994 | Matsuno | 600/107 |
| 5,423,830 | 6/1995 | Schneebaum et al. | 606/115 |
| 5,749,889 | 5/1998 | Bacich et al. | 600/135 |

FOREIGN PATENT DOCUMENTS

59-48601  3/1984  Japan .

*Primary Examiner*—Linda C. M. Dvorak
*Assistant Examiner*—Brad C. Blaise
*Attorney, Agent, or Firm*—Frishauf, Holtz, Goodman, Langer & Chick, P.C.

[57] ABSTRACT

The present invention provides an endoscope having an opening of a channel tube retracted from a distal end face having an observation window of the insert therein toward a proximal end side. When a plurality of polyps are removed, a picked-up polyp is moved back from the distal end face of the insert toward the proximal side of the insert in order for the picked-up polyp not to interfere with observation by the endoscope and operation by a cutting tool extending through the endoscope channel.

25 Claims, 8 Drawing Sheets

ENDOSCOPE

BACKGROUND OF THE INVENTION

The present invention relates to an enddscope having a channel for guiding an operating tool such as forceps to be used in removing a foreign body in the body cavity.

As is known in Jpn. UM. Appln. Publication No. 59-48601, an endoscope has a tube externally attached thereto. The tube has a channel for passing an operating tool therethrough and used by attaching it to the main body as occasion requires. The externally-provided tube extends from the control section of the endoscope to a distal end of an insert. The external tube is attached to the insert in such a way that the distal end face of the insert forms the same plane as that of the distal end face of the external tube. When the operating tool is inserted through the tube channel, a distal end of the operating tool is abutted against an observation window formed at the distal end face of the endoscope insert.

When a polyp is removed by using the endoscope thus constructed, if the foreign body is picked up by a foreign-body removing tool inserted through the external tube, the polyp is inevitably positioned in front of the distal end of the endoscope, narrowing the observation field and working area for the operating tool. Hence, in general, once the foreign-body removing tool grabs a polyp, it is difficult to cut away another polyp. As a result, the entire endoscope has to be removed out of the body every time the pick-up tool grabs a polyp.

BRIEF SUMMARY OF THE INVENTION

An object of the present invention is to provide an endoscope capable of continuously cutting or picking up a plurality of polyps present in the body cavity by means of an operating tool while leaving the endoscope in the body during a series of cutting-out operations for plurality of polyps, without removing the endoscope in every cutting operation.

According to the present invention, there is provided an endoscope having at least one endoscope channel and an observation window in the distal end portion. The opening of the at least one endoscope channel is arranged at a position longitudinally retracted from a position of the observation window toward the proximal end.

When a plurality of polyps are excised or removed from the body cavity by use of the endoscope of the present invention, the previously picked-up foreign body or the like can be retracted and stored at a position recessed from the distal end of the endoscope insert toward the proximal end. It is therefore possible to ensure the observation field and working area for the operating tool without hindrance from the previously picked-up foreign polyp and the operating tool. As a result, an additional cutting-out operation under endoscope observation can be continuously performed without removing the endoscope out of the body (with leaving the endoscope in the body cavity) by inserting another operating tool through the endoscope channel.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiment 1

Figure 1:
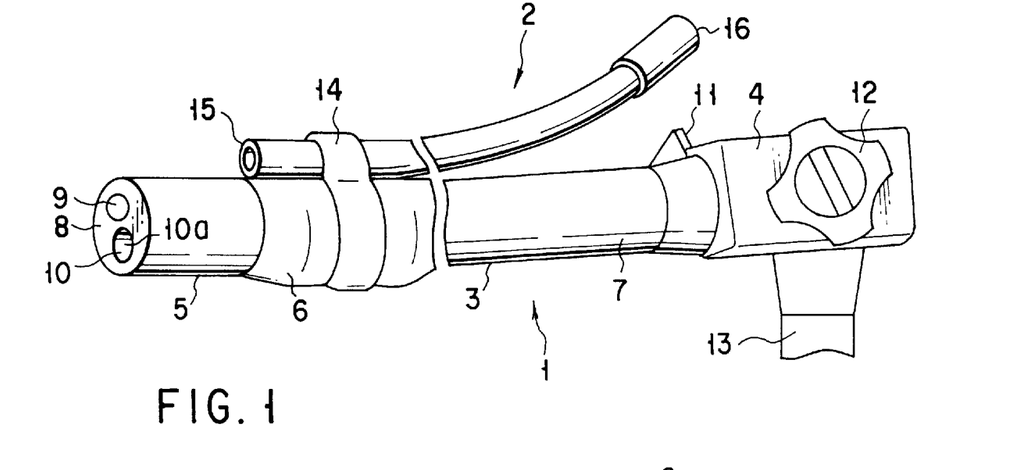
FIG. 1 is a perspective view of a channel tube provided on the exterior of an endoscope main body according to Embodiment 1 of the present invention.
Figure 2A:
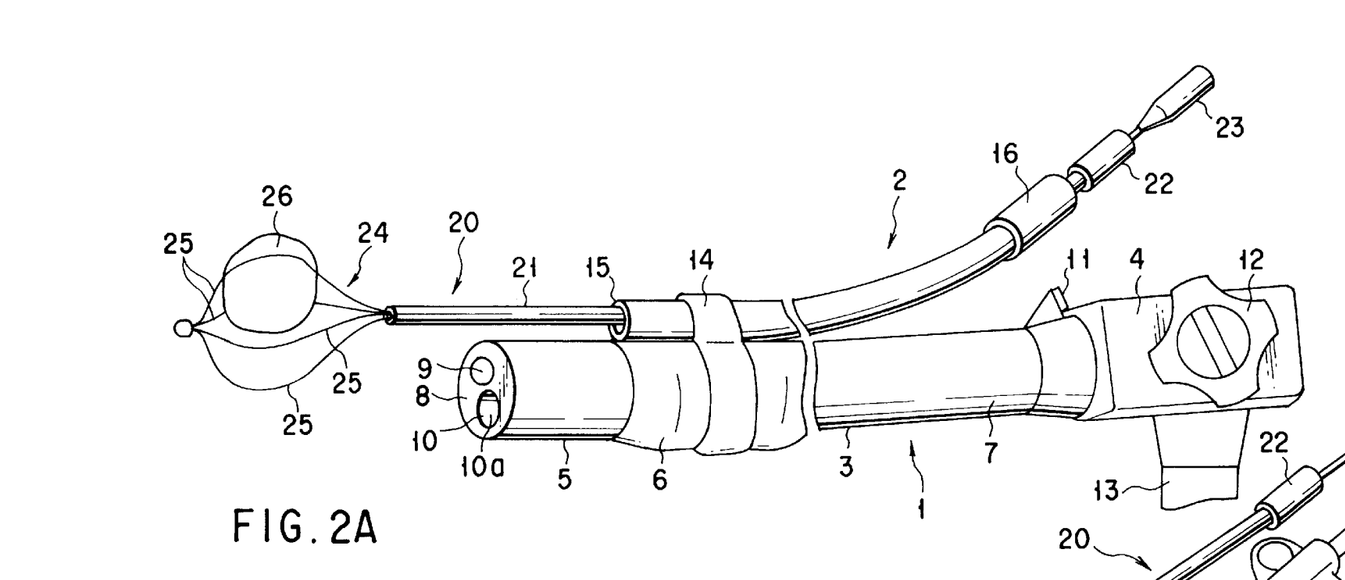
FIGS. 2A and 2B explain how to operate an endoscope having the channel tube of Embodiment 1 provided on the exterior of the endoscope main body.
Figure 2B:
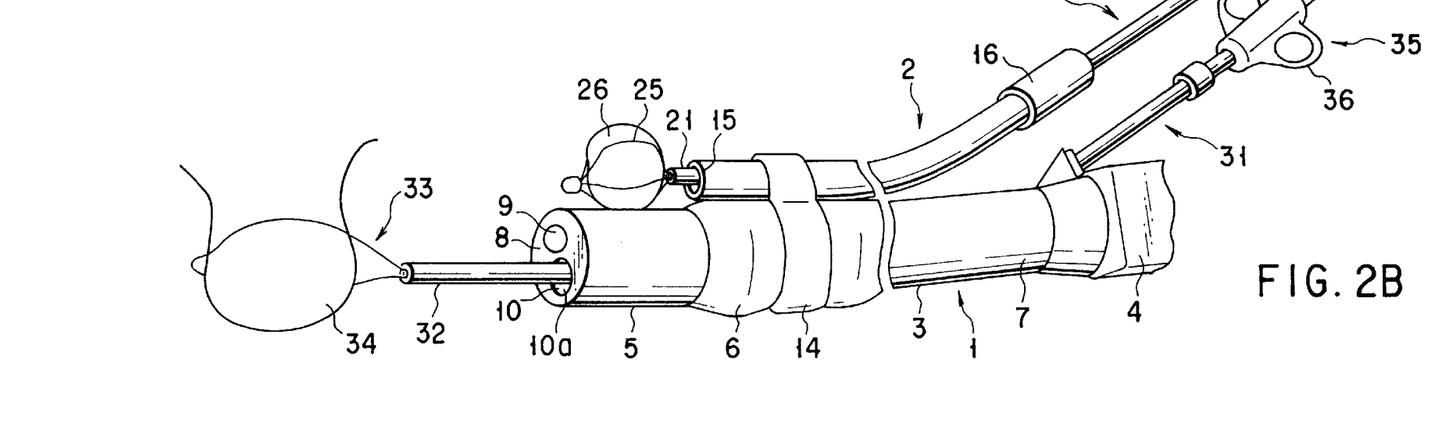

Referring to FIGS. 1, 2A and 2B, Embodiment 1 will be explained. In FIG. 1, reference numeral 1 indicates an endoscope. The endoscope 1 has a main body and a channel tube 2 discretely provided on the exterior of the main body. The main body of the endoscope 1 consists of an insert 3 and a proximal control section 4. The insert 3 is constituted of a distal-end portion 5, a bendable portion 6, and a flexible tube portion 7, arranged sequentially from the distal end side. An observation window 9 is formed in the distal-end face 8 of the distal-end portion 5. The observation is made directly through the observation window 9 of the optical observation system. In the distal-end face 8 of the distal-end portion 5, exposed is a distal-end opening portion 10a of an endoscope channel 10 formed longitudinally within the insert 3 of the endoscope 1. Other than the distal-end opening portion 10a, a lighting window and a nozzle (not shown) are formed in the distal end face 8.

The proximal control section 4 consists of an inlet 11 for inserting an operating tool and an angle knob 12. The inlet 11 is communicated with the endoscope channel 10. The angle knob 12 is responsible for bending-manipulating the bendable portion 6. A light guide cable 13 is connected to the proximal control section 4.

The external channel tube 2 is a flexible tube member thinner in diameter than the insert 3 and therefore capable of bending relatively flexibly. The channel tube 2 is set longitudinally along the insert 3 of the endoscope 1 and in contact with the upper face portion thereof.

The distal end portion of the channel tube 2 is set at the position from which the bendable portion 6 of the insert 3 is started and fixed with a rubber band bandaged around them. An opening 15 at a distal end side (opening end face) of the channel tube 2 is set at a position retracted longitudinally from the distal end face 8 of the distal end portion 5 of the insert 3 toward the proximal side. More specifically, the distal end opening portion 15 is set at a position retracted by 5 mm or more from the distal-end face 8 toward the proximal side of the endoscope 1. The opening portion 15 of the channel tube 2 is directed forward of the insert 3. The end face having the opening portion 15 formed therein is in a different plane from the distal end face 8 having the observation window 9 formed therein, but arranged in parallel.

Furthermore, an inlet 16 for inserting an operating tool is formed in a proximal end face of the channel tube 2. The inlet 16 is arranged in the vicinity of the proximal control section 4 of the endoscope 1.

The channel tube 2 is formed of a resin material relatively soft and flexible. Examples of the resin material include TEFLON (trademark), porous TEFLON (trademark), a fluorine resin such as polyethylene fluoride, vinyl chloride, urethane, and the like.

Now, we will explain how to operate the endoscope 1. As shown in FIG. 1, the channel tube 2 is externally attached to the insert 3 of the endoscope 1. The insert 3 assembled with the channel tube 2 is then inserted into the body cavity. Subsequently, a tube sheath 21 of a basket-type foreign-body removing tool 20 (serving as a foreign-body removing means) is inserted into the channel tube 2. A distal end portion of the tube sheath 21 is allowed to protrude from the distal end opening portion 15 of the channel tube 2 into the body cavity. More specifically, an operation knob 23 of a control section 22 (set at proximal side of the basket-type foreign-body removing tool 20) is moved forward, thereby moving an operation wire (not shown) through the tube sheath 21. In this :manner, a basket 24 connected at a tip portion of the operation wire is allowed to protrude from the distal end opening portion 15 of the tube sheath 21. The basket 24 has a plurality of flexible wires 25 whose distal ends and proximal ends are separately connected into one. When the basket 24 protrudes from the distal end opening portion 15 of the tube sheath 21, the basket 24 is opened due to elastic restitutive force inherent in each of elastic wires.

Then, a first polyp 26 previously excised by a cutting tool is taken into the basket 24 from an enlarged slit of the elastic wires 25 of the basket 24, as shown in FIG. 2A.

Subsequently, the tube sheath 21 of the foreign-body removing tool 20 is retracted while the first polyp 26 is kept in the basket 24, as shown in FIG. 2B. In this way, the basket 24 is moved backward from the distal end face 8 of the distal end portion 5 to the opening portion 15 of the channel tube 2. Since the basket 24 holding the polyp 26 is moved backward from the observation window 9 to the proximal end side, the field of vision of the observation window is not hindered by the basket 24 and the first polyp 26. Furthermore, it is possible to ensure a sufficient working area for another operating tool extended from the distal-end opening 10a through the channel 10 of the endoscope main body 10. Thereafter, a tube sheath 32 of a high-frequency snare (cutting tool) is inserted by passing it through the channel 10 from the operating-tool inserting inlet 11 of the endoscope 1, and then the distal end portion of the tube sheath 32 is allowed to protrude from the distal end opening 10a. Subsequently, a loop-wire form cutting portion 33 catches the root of a second polyp 34.

Then, a slider 36 of the proximal control section 35 is retracted, thereby tying up the second polyp 34 with the wire cutting portion 33. A high-frequency current is then supplied to the wire cutting portion 33, thereby cutting out the second polyp 34.

After the wire cutting portion 33 of the high frequency snare 31 is moved back, the basket-type foreign-body removing tool 20 is again moved forward from the opening portion 15 of the channel tube 2 to pick up the excised second polyp 34 into the basket 24 in the same manner as mentioned above. The basket-type foreign-body removing tool 20 is removed from the body together with the insert 3 of the endoscope 1 while keeping two polyps 26 and 34 in the same basket. In this manner, the polyps 24 and 34 are removed from the body.

The externally-provided channel tube 2 is advantageous since it can be readily used together with a conventionally-employed endoscope and operating tools. As previously described, the basket-type foreign-body removing tool 20 holding a plurality of polyps 26 and 34 is moved backward from the distal end face 8 of the endoscope 1 toward proximal end side up to the vicinity of the end opening portion 15 of the channel tube 2. It is therefore possible to prevent the polyps 26, 34 and the basket 24 from interfering with the field of vision and the working area of another operating tool (e.g., the high-frequency snare 31). In other words, observation can be made by the endoscope 1 without any hindrance, at the same time another operating tool (e.g., a cutting tool operated through the endoscope channel 10) can be manipulated without any difficulty. Hence, a plurality of polyps can be cut and picked up into the basket in a consecutive manner without removing the endoscope 1 from the body.

Embodiment 2

Figure 3A:
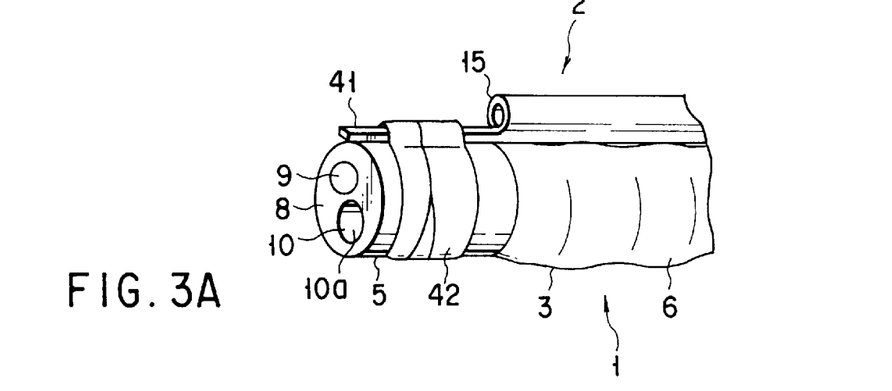
FIG. 3A is a perspective view of a channel tube provided on the exterior of an endoscope main body, according to Embodiment 2 of the present invention.
Figure 3B:
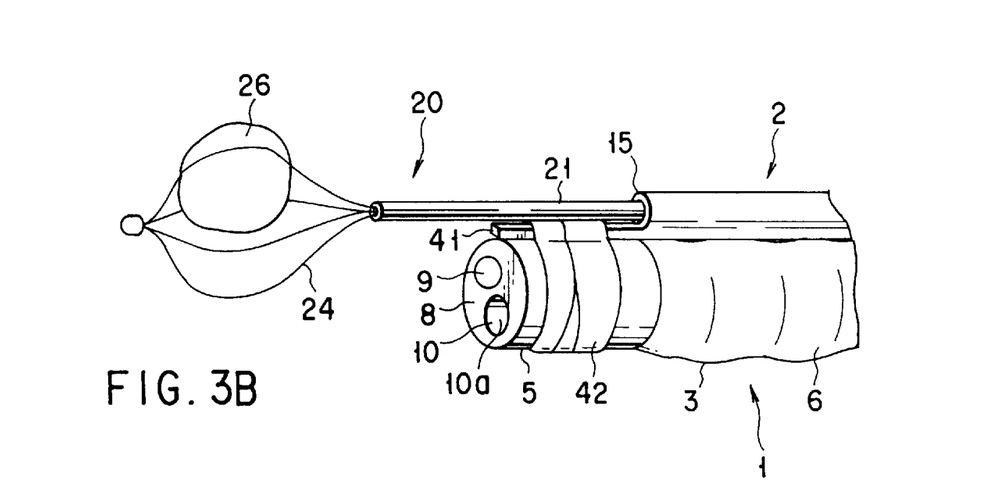
FIG. 3B explains how to operate the externally provided channel tube according to Embodiment 2.

Referring to FIGS. 3A and 3B, Embodiment 2 will be explained. The endoscope of Embodiment 2 differs from Embodiment 1 in structure of a connecting member for connecting the channel tube 2 to the exterior of the insert 3 of the endoscope 1, as follows.

In Embodiment 2, the channel tube 2 is fixed at the distal end portion 5 of the insert 3 of the endoscope 1. To be more specific, as shown in FIG. 3A, a tongue-shaped fitting piece 41 (protruding forward) is provided on a lower periphery of the distal end opening portion 15 of the channel tube 2. The tongue piece 41 is extended along the outer peripheral face of the distal end portion 5 of the endoscope 1 and fixed onto the distal end portion 5 with a fixing tape 42. An adhesive tape is particularly desirable for the fixing tape 42. The distal opening portion 15 of the channel tube 2 is arranged at a portion longitudinally retracted from the distal end face 8 toward the proximal end side of the endoscope 1.

The endoscope of Embodiment 2 can be used in the same manner as in Embodiment 1. FIG. 3B shows the state that the first polyp 26 is picked up in the basket 24 by extending the basket 24 of the basket-type foreign-body removing tool 20 from the channel tube 2.

According to Embodiment 2, the following effects can be obtained in addition to those of Embodiment 1. Since the tongue piece 41 provided on the distal end of the channel tube 2 is extended along the distal end portion 5 of the insert 3 and fixed by bandaging them with the fixing tape 42, it is easy to align the distal end opening portion 15 of the channel tube 2 with the distal end face of the endoscope 1. In addition, the channel tube 2 can be connected to the main body in a simple manner. As a result, the channel tube 2 can be fixed to the endoscope main body without fail. Furthermore, when the channel tube 2 is attached to the endoscope main body, the channel tube 2 is not directly fixed to the main body and bandaged to the tongue-shaped piece 41 extending from the distal end of the channel tube 2 with the fixing tape 42. By virtue of this structure, the channel portion will not be squeezed by fastening tight when the channel tube 2 is assembled with the insert 3.

Embodiment 3

Figure 4A:
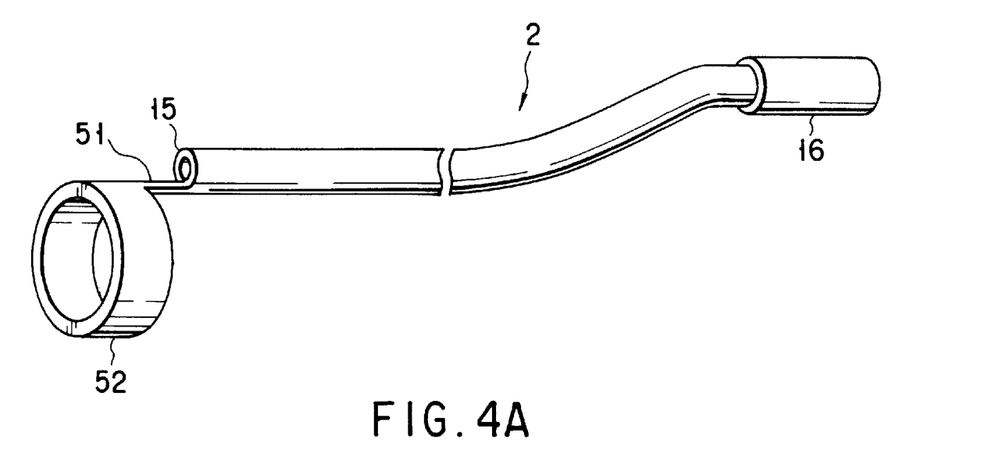
FIG. 4A is a perspective view of the externally-provided channel tube according to Embodiment 3 of the present invention.
Figure 4B:
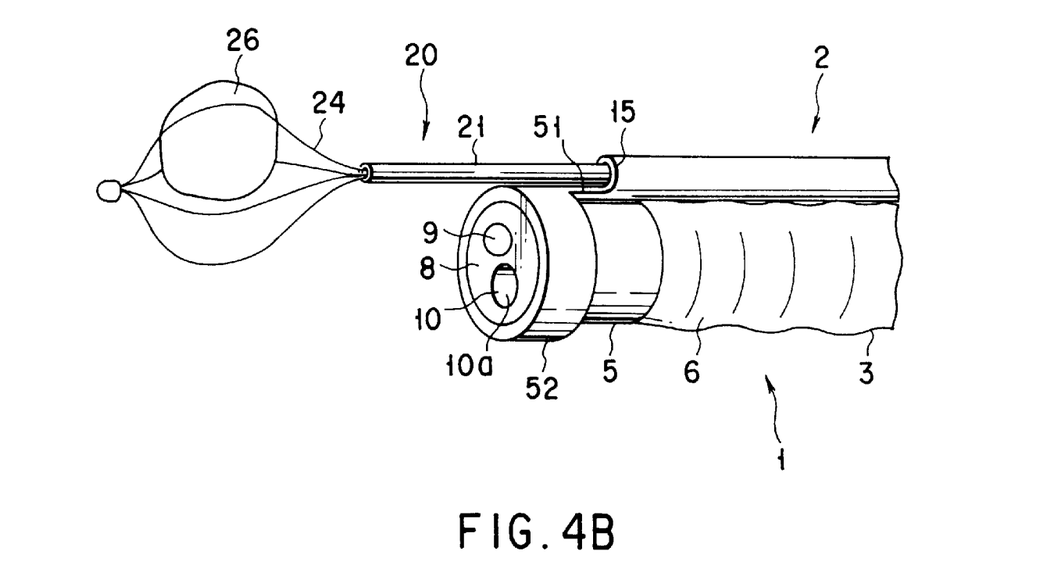
FIG. 4B explains how to operate the externally-provided channel tube according to Embodiment 3.

Referring to FIGS. 4A and 4B, Embodiment 3 will be explained. Embodiment 3 is a modified example of Embodiment 1 and characterized in a connecting structure for attaching the channel tube 2 to the exterior of the insert 3 of the endoscope 1.

In Embodiment 3, a protruding portion 51 (projecting forward) is provided on a lower portion of an distal-end opening of a channel tube 2, as shown in FIG. 4A. Furthermore, a short-length cylindrical fixing cap 52 is attached to a tip portion of the protruding portion 51. In other words, the fixing cap 52 is located at a lower level than the distal end of the channel tube 2 and engages tight with the outer periphery of the distal end portion 5 of the insert 3.

As shown in FIG. 4B, the channel tube 2 is fixed at the distal end portion 5 by engaging the fitting cap 52 with the distal end portion 5 of the insert 3. The fixing cap 52 is detachable to the distal end portion 5.

In Embodiment 3, since the channel tube 2 can be fixed at the insert 3 of the endoscope 1 by engaging the fitting cap 52 to the distal end portion 5 of the insert 3, another fitting member is not required. In addition, the fitting cap 52 can be fixed in a simple manner.

Embodiment 4

Figure 5A:
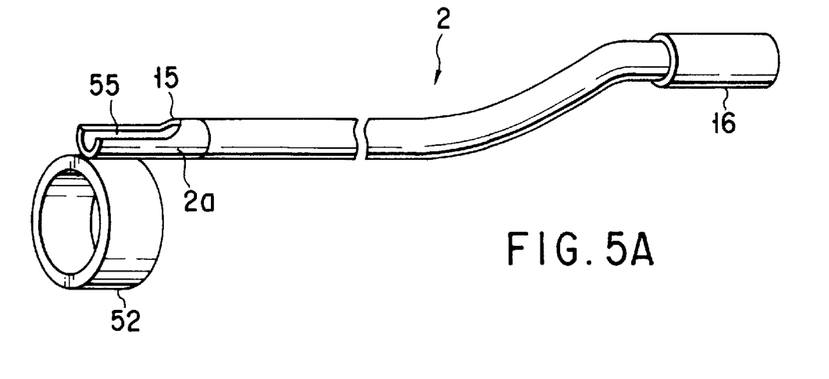
FIG. 5A is a perspective view of an externally-provided channel tube according to Embodiment 4 of the present invention.
Figure 5B:
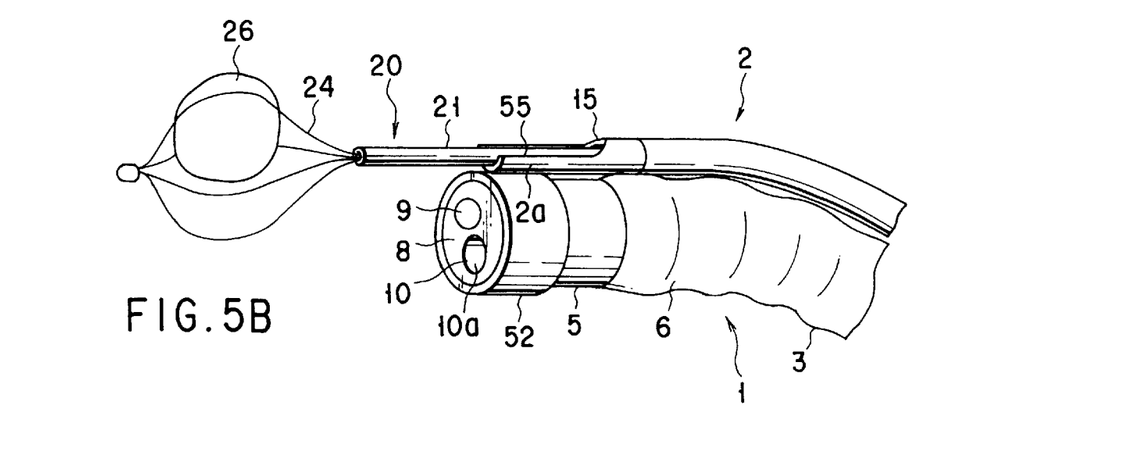
FIGS. 5B and 5C explain how to operate the channel tube according to Embodiment 4.
Figure 5C:
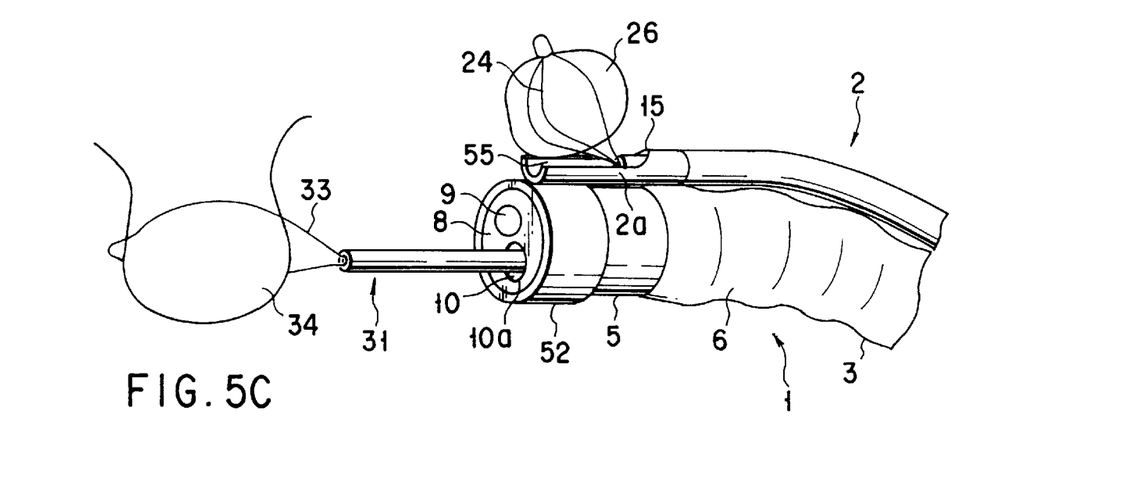

Referring to FIGS. 5A to 5C, Embodiment 4 will be explained. Embodiment 4 is a modified example of Embodiment 3.

In Embodiment 4, a hard portion 2a is formed at the distal end portion of the channel tube 2 as shown in FIG. 5A. The cap 52 formed of a different material is fitted to a lower face of a tip portion of the hard portion 2a. The cap 52 can be detachably fitted to the distal end portion 5 of the endoscope 1, as shown in FIG. 5B. The upper side of the hard portion 2a, which is an opposite side facing the cap 52, is partially cut away, thereby forming a guide groove 55. Therefore, the distal end opening portion 15 of the channel tube 2 is set at a position retracted from the guide groove 55 toward the proximal side, in other words, set at the proximal-side portion of the hard portion 2a.

FIGS. 5B and 5C show how to use the endoscope. In FIG. 5B, a first polyp 26 is taken into the basket 24 extending from the channel tube 2. In FIG. 5C, the basket 24 holding the first polyp 26 is moved backward and a wire cutting portion 33 of the high-frequency snare 31 is extended through the channel 10 of the endoscope, thereby catching the root of a second polyp 34. The second polyp 34 is tied up with the wire cutting portion 33 by retracting a slider 36 of the proximal control section 35. A high frequency current is then supplied to the wire cutting portion 33 to excise the second polyp 34.

In Embodiment 4, the channel tube 2 is fitted to the endoscope 1 by engaging the cap 52 with the distal end portion 5 of the endoscope 1 in the same manner as in Embodiment 3.

When the basket-type foreign-body removing tool 20 is allowed to protrude or retract from the body cavity through the channel tube 2, a tip of the tube sheath 21 is guided along the guide groove 55. Even if the bendable portion 6 of the endoscope bends, the tube sheath 21 is successfully guided in the direction in parallel to the longitudinal axis of the insert 3 of the endoscope 1. The tube sheath 21 can be ensured to move back and forth.

Embodiment 5

Figure 6A:
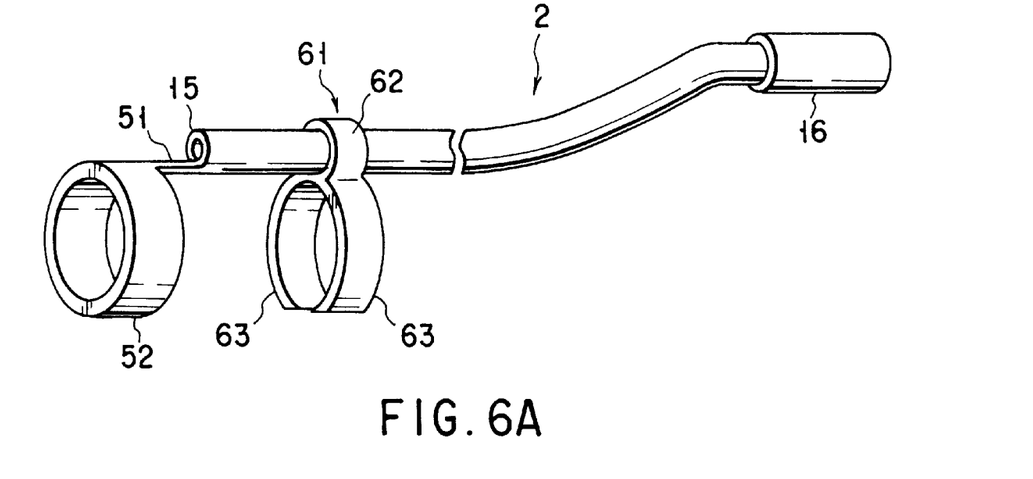
FIG. 6A is a perspective view of an externally provided channel tube according to Embodiment 5 of the present invention.
Figure 6B:
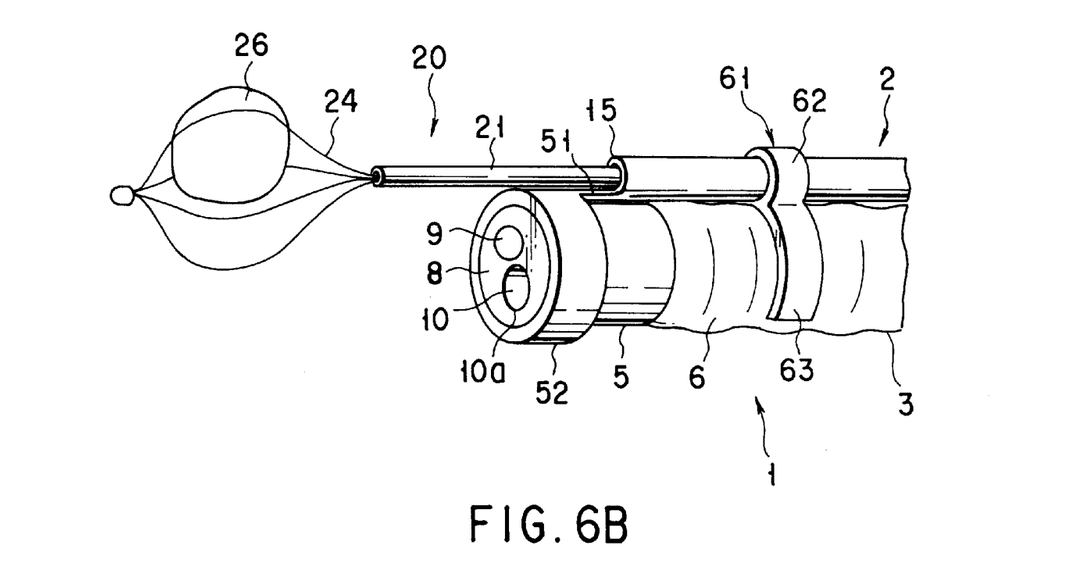
FIG. 6B explains how to operate the endoscope having the channel tube according to Embodiment 5 provided on the exterior of the endoscope main body.

Referring now to FIGS. 6A and 6B, Embodiment 5 will be explained. Embodiment 5 is a modified example of Embodiment 3.

In this embodiment, a fixing clip 61 is provided in close vicinity of the distal end of the channel tube 2. The fixing clip 61 consists of a ring-shaped proximal portion 62 attached to the channel tube 2 and a pair of holding pieces 63 for sandwiching the bendable portion 6 of the insert 3 of the endoscope 1. The members 62 and 63 are contiguously formed in one body. When the channel tube 2 is attached to the endoscope main body, the fixing cap 52 of the channel tube 2 is engaged with the distal end portion 5 of the insert 3; at the same time, the holding pieces 63 of the fixing clip 61 sandwich the bendable portion 6 of the insert 3. The channel tube 2 is attached to the endoscope main body by not only the fixing cap 52 but also the fixing clip 61. According to Embodiment 5, the channel tube 2 can be attached to the exterior of the insert 3 in a one-touch operation without fail.

Embodiment 6

Figure 7A:
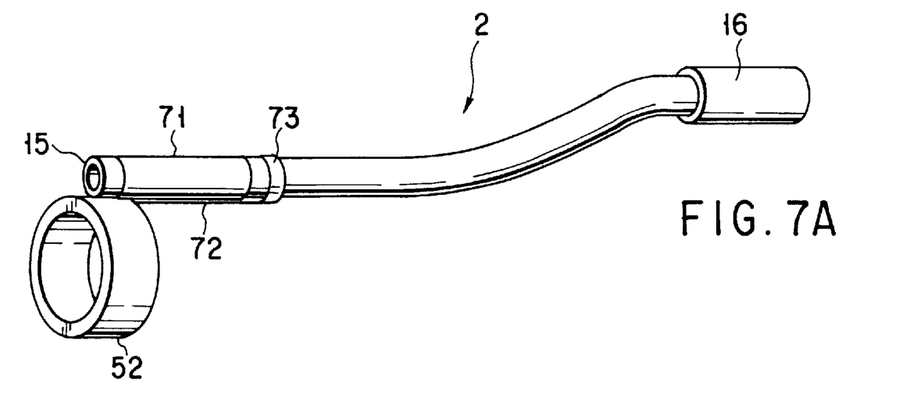
FIG. 7A is a perspective view of an externally provided channel tube according to Embodiment 6 of the present invention.
Figure 7B:
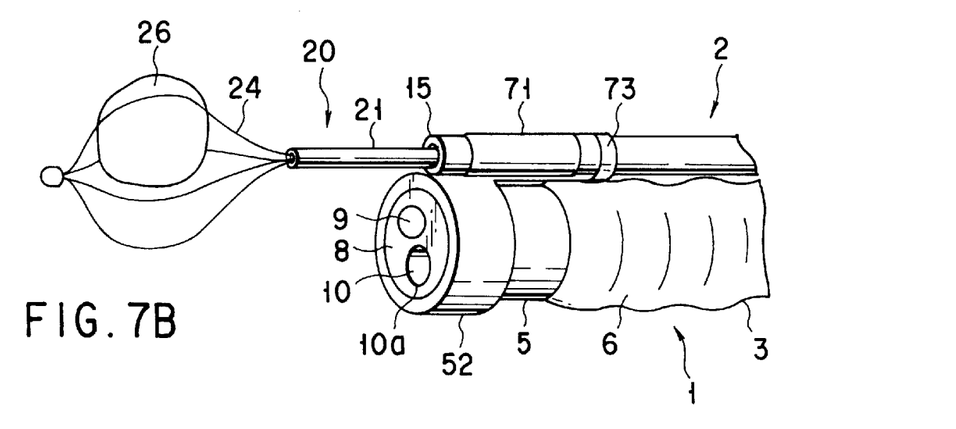
FIGS. 7B and 7C explain how to operate the channel tube according to Embodiment 6.
Figure 7C:
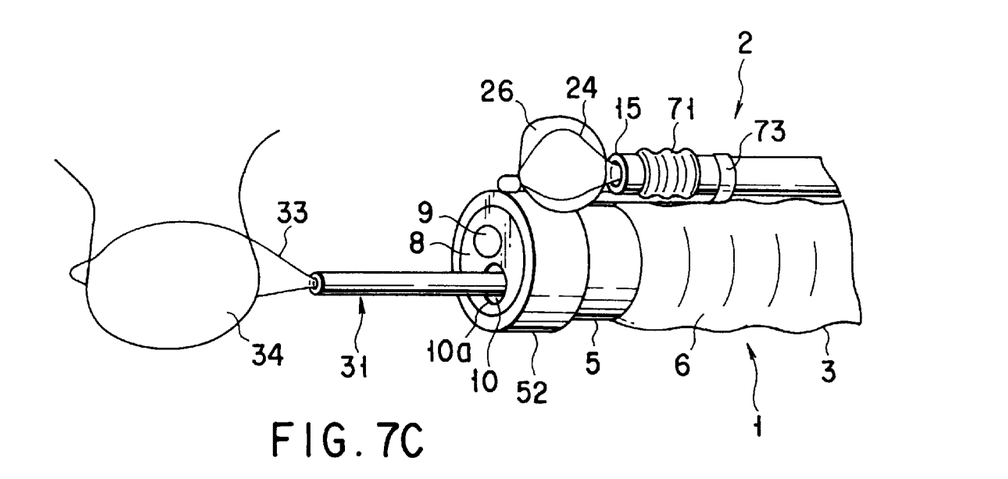

Referring to FIGS. 7A to 7C, Embodiment 6 will be explained. Embodiment 6 is a modified example of Embodiment 3.

In Embodiment 6, a tube-shape elastic portion 71 is provided in a close proximity with the distal end of the externally-provided channel tube 2, as shown in FIG. 7A. The elastic portion 71 has the same diameter as the channel tube 2 and is extensible in the longitudinal direction of the channel tube 2. Since the distal end opening portion 15 of the channel tube 2 is formed at a distal end side of the elastic portion 71, the distal-end opening 15 can be moved back and forth in the axis direction, accordingly.

The elastic portion 71 has a bellows-like structure and is formed of either the same material (e.g., fluorine resin such as Teflon (trade name)) as used in the reminder part of the channel tube 2 or a softer material (e.g, a lower-density material) than the reminder part of the channel tube 2.

In addition, a fixing ring 73 is provided on the fixing cap 52 by way of a connecting piece 72. The fixing ring 73 is attached so as to engage with the periphery of the distal end portion of the channel tube 2 at a position retracted from the elastic portion 71 toward the proximal side. The fixing ring 73 is fitted to the outer periphery of the distal end portion 5 of the insert 3. In this manner, the fixing cap 52 is attached to the endoscope 1.

Now, we will explain the case in which the channel tube 2 of this type is used by attaching to the endoscope 1. The basket-type foreign-body removing tool 20 is extended through the channel tube 2 as shown in FIG. 7B, the elastic portion 71 of the channel tube 2 is elongated forwards while leaving the distal end opening portion 15 of the channel tube 2, in the vicinity of the distal end face 8 of the distal end portion 5 of the endoscope 1. It is therefore possible to prevent wobbling of the basket-type foreign-body removing tool 20 extending from the distal-end opening portion 15. As a result, the foreign-body pick-up basket 21 can be operated more easily.

On the other hand, while the first polyp 26 is being grabbed by the basket 24 of the foreign-body removing tool 20, the tube sheath 21 is pulled to retract the basket 24. At this time, the elastic portion 71 which has been longitudinally extended forward is pressed by the basket 24, thereby contracting. As a result, the basket 24 is retracted from the distal face 8 of the distal portion 5 toward the proximal-end portion. Since the basket 24 holding the first polyp 26 is retracted from the distal face 8 of the distal end portion 5 toward the proximal-end portion, the polyp 26 and the basket 24 do not interfere with the field of vision through the observation window 9 and the working area of the cutting portion 33 of the high frequency snare 31.

Embodiment 7

Referring to FIGS. 8A to 8D, Embodiment 7 of the present invention will be explained. Embodiment 7 shows a modified example of the basket-type foreign-body removing tool 20 shown in Embodiment 1.

Figure 8A:
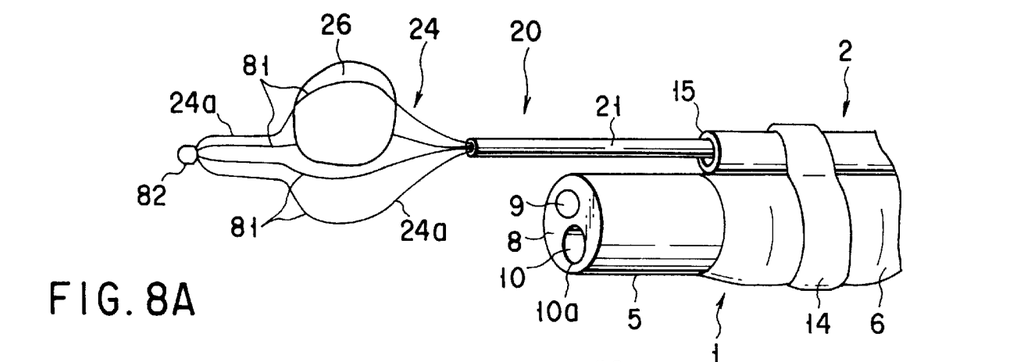
FIGS. 8A to 8D explain how to operate a basket type foreign-body removing tool in the endoscope according to Embodiment 7 of the present invention.

The basket-type foreign-body removing tool 20 has a basket 24 whose elastic wires 81 are bundled at a tip portion with a distal-end tip 82. Each proximal end of the elastic wires is inserted into the tube sheath 21 and connected to an operation wire (not shown) passing through the tube sheath 21. By virtue of this structure, the proximal end of each of the elastic wire 81 is introduced into and protrude from the tube sheath 21. The basket 24 has an intake portion 24a capable of enlarging larger than the reminder portion due to its restitutive force. On the other hand, a store portion 24b is formed narrow in the distal end portion of the basket 24, compared to the intake portion 24a.

Figure 8B:
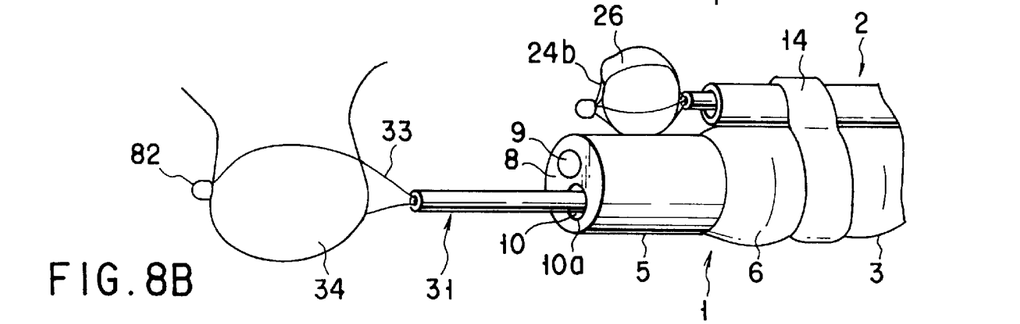

When the basket-type foreign-body removing tool 20 is used, the first polyp 26 is first taken into the intake portion 24a by passing it through a slit between elastic wires 81, as shown in FIG. 8A. Second, the operation wire of the basket-type foreign-body removing tool 20 is pulled to withdraw the intake portion 24a into the tube sheath 21, as shown in FIG. 8B. With this movement, the first polyp 26 is pushed into the distal end side of the store portion 24b and stored therein. Thereafter, the tube sheath 21 is pulled into the channel tube 2 and the basket 24 storing the first polyp 26 is withdrawn to a side portion of the distal end portion 5 of the insert 3, as shown in FIG. 8B.

Figure 8C:
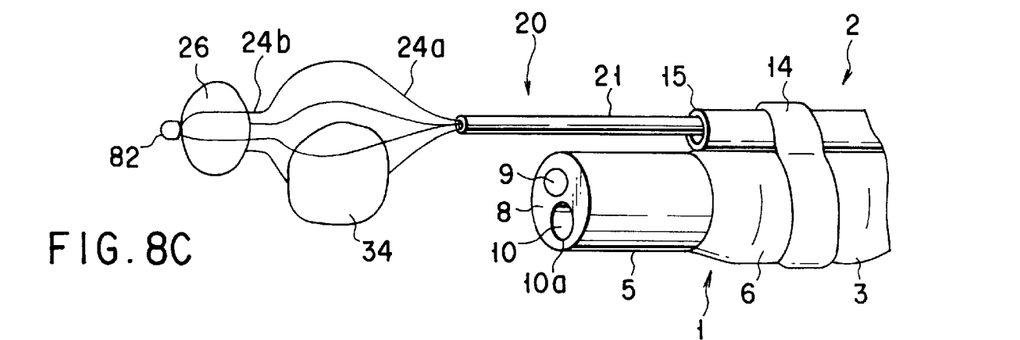
Figure 8D:
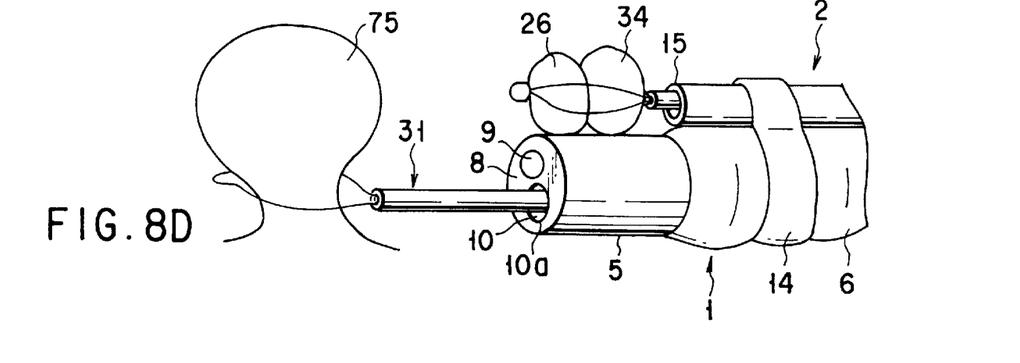

When the second polyp 34 is removed, the basket 24 of the foreign-body removing tool 20 is again pushed forwards. Then, the interval between wires of the basket 24 is enlarged to intake the second polyp 34, as shown in FIG. 8C. Subsequently, the basket type foreign-body removing tool 20 is pulled bakeds into the channel tube 2 in the same manner as mentioned as shown in FIG. 8D. Consequently, the second polyp 34 is taken into the store portion 24b of the basket 24, and simultaneously withdrawn to the side of the distal end 5 of the insert 3.

The same procedure is repeated to store a third polyp 75 into the store portion 24b of the basket 24. In the manner mentioned, first, second and third polyps 26, 34, 75 are stored sequentially from the distal end. According to this embodiment, additional advantages are presented other than those of embodiments set forth above. First, a plurality of polyps can be stored simultaneously in the basket 24 without removing the basket-type foreign-body removing tool out of the body. Second, since polyps are stacked in the order of charging, it is possible to know which polyp is cut first or second. Hence, it is advantageous in distinguishing and examining them.

Embodiment 8

Figures 9A, 9B:
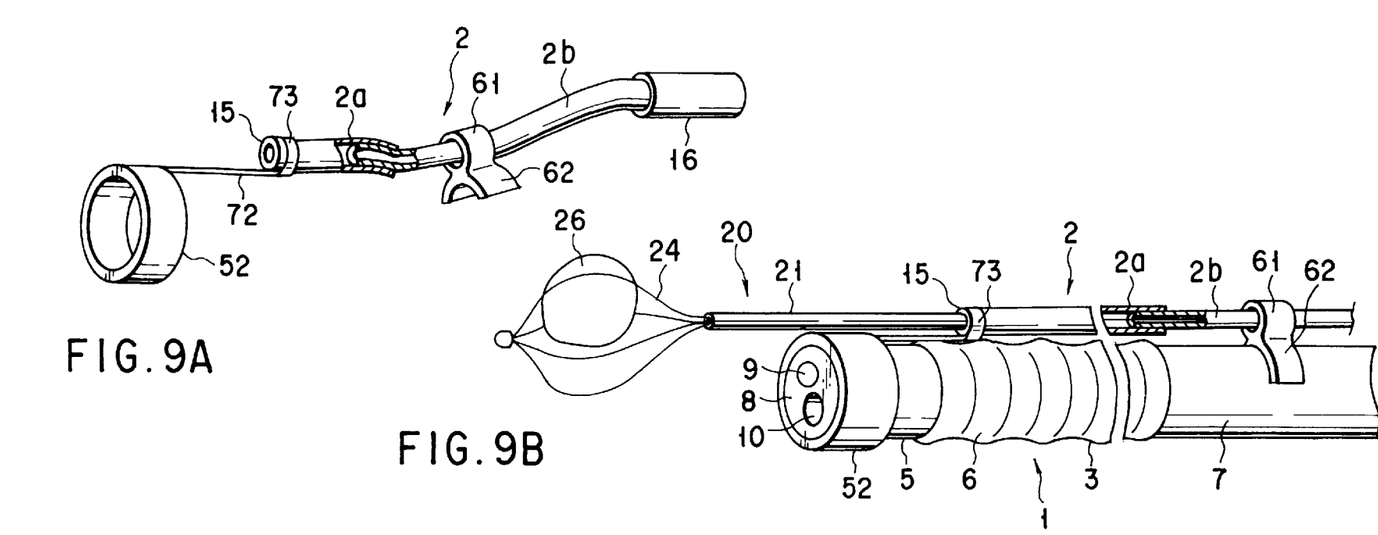
FIG. 9A is a perspective view of the externally provided channel tube according to Embodiment 8 of the present invention.
FIG. 9B explains how to operate the externally-provided channel tube according to Embodiment 8.

Referring to FIGS. 9A and 9B, Embodiment 8 will be explained. Embodiment 8 is a modified example of Embodiment 6.

A tube corresponding to the externally-provided channel tube 2 of Embodiment 6 is herein constituted of two tubes, namely, an outer tube 2a (positioned at the distal end side) and an inner tube 2b (positioned at the rear end side). More specifically, the tip portion of the inner tube 2b is inserted tight into the base portion of the outer tube 2a positioned at the distal end side of the channel tube, so that they are fitted and connected to each other slidably in the axial direction. By forming the channel tube 2 of these two tubes, the channel tube 2 can be extended in the axis direction. It is desirable that the channel tube 2 should be extended in the axis direction within the range of 40 to 80 mm. If so, the channel tube can be adapted to all surgical endoscopes even if its bendable portion 6 of the insert 3 is bent to any extent. Furthermore, a stopper (not shown) is provided between the outer tube 2a and the inner tube 2b to thereby prevent the tubes 2a and 2b from being separate from each other.

The fitting cap 52 is connected to the fixing ring 73 via the connecting piece 72 to fit them unmovablly. The fixing ring 73 is engaged with the outer periphery of the outer tube 2a to fit them unmovably. As a result, the fitting cap 52 is fixed to the outer tube 2a via the connecting piece 72 and the fixing ring 73.

Furthermore, a ring-shape fixing clip 61 is engaged with the inner channel tube 2b in the vicinity of the distal end. The fixing clip 61 is attached to the inner channel tube 2b slidably in the axis direction.

Note that the fixing clip 61 is formed of a cured resin such as vinyl chloride and may be formed of a soft resin such as urethane and silicone or a metal such as stainless. Any configuration, (e.g., thin-film (tape) form and a spiral coil) may be employed as the fitting clip 61 as long as it can be attached slidably to the outer periphery of the inner tube 2b.

Now, we will describe the case in which the externally provided channel tube 2 of this embodiment is used.

In the first place, the fitting cap 52 is engaged with the outer periphery of the distal end portion 5 of the insert 3 of the endoscope 1. Then, a pair of sandwiching pieces 63 of the fixing clip 1 are engaged with the flexible tube 7 of the insert 3. In this way, the external channel tube 2 is attached to the endoscope main body. If necessary, the outer tube 2a located at a position retracted from the fixing clip 61 may be fixed to the flexible tube 7 of the insert 3 with a surgical tape (not shown).

As mentioned, the insert 3 of the endoscope 1 integrated with the external channel tube 2 is introduced into the body cavity.

In this embodiment, the outer tube 2a and the inner tube 2b are connected to each other slidably in the axis direction. In addition, the fixing clip 61 is slidably engaged with the outer periphery of the inner tube 2b. It is therefore possible to extend the externally-provided channel tube 2 in the axial direction even if the insert of the endoscope 1, particularly, the bendable portion 6, is bendable significantly. The external channel tube 2 can be extended in the axis direction in accordance with the bend of the insert 3 of the endoscope 1. Hence, the insert 3 can be bent smoothly without preventing the movement of the insert 3.

Embodiment 9

Figure 10:
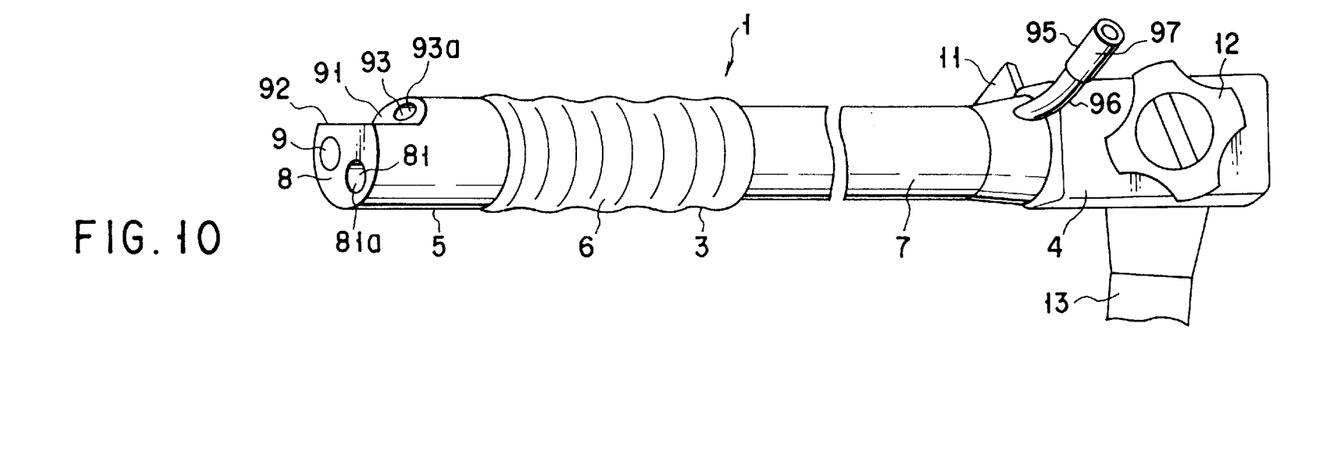
FIG. 10 is a perspective view of an endoscope according to Embodiment 9 of the present invention.

Referring to FIG. 10, Embodiment 9 will be explained. In Embodiment 9, all endoscope channels are formed within the endoscope main body.

The main body of the endoscope 1 has an insert 3 and a control section 4 at the proximal sickle. The insert 3 is constituted of a distal end portion 5, a bendable portion 6 and a flexible portion 7 arranged sequentially from the distal end side. In the distal end face 8 of the distal end portion 5 of the insert 3, an observation window 9 of the optical system and an distal-end opening 81a of an endoscope channel 81 are formed. Other than the aforementioned members, a lighting window and a nozzle (not shown) are formed in the distal end face 8 of the insert 3.

The control section 4 has an operating-tool inserting inlet 11 communicated with the endoscope channel 81 and an angle knob 12 for operating the bendable portion 6. A light guide cable 13 is connected to the proximal control section 4. The construction of the endoscope 1 mentioned above is the same as shown in Embodiment 1.

In the distal end portion 5 of the insert 3 between the distal end face 8 and the bendable portion 6, an upper portion of the insert is partially cut away by a length of 8 to 10 mm from the distal end side, thereby forming a stepped and recessed portion 92. As a result, additional distal end portion 91 is formed which is inclined backward (rearward) at an angle of 90° or less with respect to the distal end face 8 of the distal end portion 5, more specifically, at an angle of 45.

In the distal end face 91, a distal end opening 93a is exposed which is an opening of another endoscope channel 93 different from the endoscope channel 81. The endoscope channel 93 is formed in parallel with the axial direction of the insert 3 of the endoscope 1 in the vicinity of the distal end side. Due to the structure mentioned, when an operating tool present in the endoscope channel 93 is allowed to project from the distal end opening 93a, the operating tool is extended in parallel with the axial direction of the endoscope 1, passes above the stepped portion 92 and extends forwards of the endoscope 1.

The distal end portion 91 is recessed by a distance of 10 mm from the distal end face 8 of the insert 3 in the axial direction. However, the distance desirably falls within the range of 5 to 20 mm. If the distance is less than 5 mm, when a foreign body (e.g., a polyp) caught by forceps or the basket-type foreign-body removing tool (passing through the endoscope channel 93 and extending from the distal end opening portion 93a) is moved backward, the operating tool and the foreign body will interrupt with the field of vision of the observation window 9. As a result, good observation cannot be made. In contrast, if the distance from the distal end face 8 to the distal end face 91 is larger than 20 mm, the operating tool extending from the endoscope channel 93 is prone to bend due to the gravity or external force before it reaches to the distal end portion of the insert 3. As a result, the operating tool fails in extending in the same direction of the axis of the insert 3 and tends to bend in the middle. Since the direction of the operating tool is changed variably, it becomes difficult to manipulate the operating tool as intended.

Furthermore, the distal end face 91 is inclined backwards at an angle of 45°. If the angle falls within the range 30° to 90°, the endoscope 1 can be inserted smoothly with few effects upon a mucous membrane.

The endoscope channel 91 is communicated with an inserting inlet 95 formed in the proximal control section 4 of the endoscope 1. An operating tool can be inserted into the endoscope channel 93 from the inserting inlet 95. The inserting inlet 95 is formed of an introduction tube 96 and a clasp 97. The clasp 97 has a sealing cap (not shown). The clasp 97 is usually sealed with the sealing cap. Therefore, the operating tool is inserted airtight.

Next, how to use the endoscope 1 will be explained. At first, the insert 3 of the endoscope 1 is introduced into the body cavity. Then, the basket-type foreign-body removing tool 20 is inserted through the endoscope channel 93 set sideward and allowed to protrude in the body cavity, in the same manner as in Embodiment 1. After the polyp 26 is picked up by the basket-type foreign-body removing tool 20, the basket-type foreign-body removing tool 20 having the polyp 26 is retracted until it hits the distal end face 91 while holding the polyp 26. Since the basket-type foreign-body removing tool 20 and the polyp 26 are retracted frogs the distal end face 8 to the proximal end side and placed on the stepped portion 92, they are expelled from the observation field of the endoscope 1.

Hence, a sufficient working room is ensured for another operating tool protruding from the endoscope channel 93 without hindrance from the basket-type foreign-body removing tool 20 and the polyp 26. In addition, since the distal end face 91 having a distal-end opening 93a formed therein is inclined backwards, the endoscope 1 can be smoothly inserted into the body cavity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:

an insert having a distal end portion to be inserted in an area to be observed, said distal end portion of the insert having an observation window, and said insert having a first channel therein which has a first distal end opening portion directed toward a space exterior to the endoscope and through which a first operating tool may be passed;

a second channel arranged along an axial direction of the insert, said second channel having a second distal end opening portion directed toward the space exterior to the endoscope and through which a second operating tool may be passed;

wherein said second distal end opening portion of the second channel is formed at a position retracted from the observation window toward a proximal end of the insert.

2. The endoscope according to claim 1, wherein said distal end portion of the insert comprises a first face in which said observation window is formed, and said second channel comprises a second face in which said second distal end opening portion is formed, said first and second faces being formed in different planes arranged in parallel.

3. The endoscope according to claim 1, wherein said distal end portion of the insert comprises a first face in which said observation window is formed, and said second channel comprises a second face in which said second distal end opening portion is formed, said first and second faces being formed in different planes not arranged in parallel.

4. The endoscope according to claim 1, wherein said distal end portion of the insert comprises a first face in which said observation window is formed, and said second channel comprises a second face in which said second distal end opening portion is formed, said first face being inclined at an angle of 90° or less with said second face, toward the proximal end of the insert.

5. The endoscope according to claim 1, wherein said insert has a bendable portion at a position retracted from the distal end portion of the insert toward the proximal end of the insert, and said second distal end opening portion of the second channel is arranged between a distal end of the distal end portion of the insert and the bendable portion.

6. The endoscope according to claim 1, further comprising a guide arranged in front of the second distal end opening portion of the second channel for defining an extension direction of the second operating tool when the second operating tool is passed through the second distal end opening portion of the second channel.

7. The endoscope according to claim 1, wherein said second channel is formed within a tube-form member different from the insert.

8. The endoscope according to claim 7, wherein said tube-form member is flexible.

9. The endoscope according to claim 7, further comprising a connector which connects the tube-form member to the insert.

10. The endoscope according to claim 9, wherein said connector comprises a band for binding the tube-form member to the insert.

11. The endoscope according to claim 9, wherein said connector comprises a cap for detachably attaching onto an outer periphery of the distal end portion of the insert.

12. The endoscope according to claim 9, wherein said connector comprises a clip for holding and fitting said tube-form member onto the insert by sandwiching an outer periphery of the insert.

13. The endoscope according to claim 9, wherein said connector comprises a fixing member for holding and fixing said tube-form member at the distal end portion of the insert.

14. The endoscope according to claim 9, wherein said connector comprises a member capable of holding the tube-form member at any position in the axial direction of the insert.

15. The endoscope according to claim 7, wherein said tube-form member comprises an extensible portion in an axial direction of the tube-form member, so that said second distal end opening portion of the second channel is changed in position by moving back and forth along the axial direction of the tube-form member through movement of the extensible portion.

16. The endoscope according to claim 7, wherein said tube-form member comprises an inner tube and an outer tube, both being slidable relative to each other in an axial direction of the tube-form member and both being extensible in the axial direction of the tube form-member.

17. The endoscope according to claim 1, wherein said distal end portion of the insert comprises a first face in which said observation window is formed, and said second channel comprises a second face in which said second distal end opening portion is formed, said second face being retracted from said first face toward the proximal end of the insert by a length equal to or more than a length of the distal end portion of the insert.

18. The endoscope according to claim 1, wherein said second channel is integrally formed with said insert as a single unit.

19. The endoscope according to claim 18, wherein said second distal end opening portion of the second channel is formed in a rise of a stepped and recessed portion of the single unit which is formed by partially cutting away the distal end portion of the insert.

20. The endoscope according to claim 19, wherein said distal end portion of the insert comprises a first face in which the observation window is formed, and said second channel comprises a second face in which said second distal end opening portion is formed, said second face being inclined at an angle of 90° or less with respect to the first face the proximal end of the insert.

21. The endoscope according to claim 19, wherein said distal end portion of the insert comprises a first face in which the observation window is formed, and said second channel comprises a second face in which said second distal end opening portion is formed, said second face being inclined at an angle from 30° or more to less than 90° with respect to the first face.

22. The endoscope according to claim 18, wherein said distal end portion of the insert comprises a first face in which the observation window is formed, and said second channel comprises a second face in which said second distal end opening portion is formed, said second face being inclined at an angle of 90° or less with respect to the first face toward the proximal end of the insert.

23. The endoscope according to claim 18, wherein said distal end portion of the insert comprises a first face in which the observation window is formed, and said second channel comprises a second face in which said second distal end opening portion is formed, said second face being inclined at an angle from 30° or more to less than 90° with respect to the first face.

24. An endoscope comprising:
  an insert having a distal end to be inserted in an area to be observed, said distal end portion of the insert having an observation window,
  a channel arranged along an axial direction of the insert, said channel having a distal end opening directed toward a space exterior to the endoscope and through which an operating tool for picking up a foreign body may be passed;
  wherein said distal end opening of the channel is retracted from the observation window toward a proximal end of the insert.

25. The endoscope according to claim 24, wherein said operating tool comprises a basket formed from a plurality of wires and having a foreign-body pick-up portion formed of wires whose intervals are extensible and a store portion formed of wires arranged at narrower intervals than the foreign-body pick-up portion for storing the foreign body picked up by the foreign-body pick-up portion.

* * * * *